United States Patent [19]
Kato

[11] Patent Number: 6,162,836
[45] Date of Patent: Dec. 19, 2000

[54] PROCESS FOR PREPARING AQUEOUS DISPERSION OF HIGHER FATTY ACID ZINC SALT

[75] Inventor: Yasuo Kato, Ashiya, Japan

[73] Assignee: Nissin Kagaku Kenkyusho Co., Ltd., Ehime, Japan

[21] Appl. No.: 09/321,557

[22] Filed: May 28, 1999

Related U.S. Application Data

[63] Continuation of application No. 08/729,530, Oct. 11, 1996, abandoned.

[51] Int. Cl.$^7$ .................................. B01F 3/08; C07F 3/06
[52] U.S. Cl. ................................ 516/77; 516/67; 554/75; 162/179
[58] Field of Search .................. 516/77, 67, 68, 516/69; 554/75, 156, 157; 556/131; 162/179

[56] References Cited

U.S. PATENT DOCUMENTS

| | | | |
|---|---|---|---|
| 12,361 | 2/1855 | Glynn | 162/179 |
| 989,425 | 4/1911 | Rogers | 162/179 |
| 2,985,544 | 5/1961 | De Monterey et al. | 428/447 |
| 3,305,392 | 2/1967 | Britt | 428/211 |
| 3,803,188 | 4/1974 | Scott et al. | 554/156 |
| 4,060,535 | 11/1977 | Cinco | 554/156 |
| 4,316,852 | 2/1982 | Blachford | 556/131 |
| 5,164,523 | 11/1992 | Hudson et al. | 554/75 |
| 5,191,098 | 3/1993 | Koenig et al. | 554/156 |

OTHER PUBLICATIONS

Myers, Surfactant Science andTechnology (VCH Publishers, Inc., NY, NY, copyright 1988) pp. 68–69, Jun. 1988.
Schwartz et al., *Surface Active Agents and Detergents*, vol. ll, pp. 162–163 (1958), Month unknown.

*Primary Examiner*—Richard D. Lovering
*Assistant Examiner*—Daniel S. Metzmaier
*Attorney, Agent, or Firm*—Wenderoth, Lind & Ponack, L.L.P.

[57] ABSTRACT

A process for preparing an aqueous dispersion of a higher fatty acid zinc salt which comprises adding a molten higher fatty acid to an aqueous dispersion of zinc oxide and reacting the higher fatty acid with the zinc oxide in the presence of a surfactant or a water-soluble polyvinyl alcohol with stirring while the aqueous dispersion is maintained at a temperature that is higher than the melting point of the higher fatty acid used.

8 Claims, No Drawings

PROCESS FOR PREPARING AQUEOUS DISPERSION OF HIGHER FATTY ACID ZINC SALT

This is a continuation of Ser. No. 08/729,530, filed Oct. 11, 1996, now abandoned.

BACKGROUND OF THE INVENTION

1. Field of the Invention

This invention relates to a process for preparing an aqueous dispersion of higher fatty acid zinc salt. More particularly, the invention relates to a wet direct precipitating process for preparing a low viscosity aqueous dispersion of higher fatty acid zinc salt having a small particle size in high yields.

2. Description of the Prior Art

An aqueous dispersion of a metallic soap has been heretofore produced by first preparing a metallic soap and then dispersing the metallic soap in water in the presence of a surfactant. For industrial use, the metallic soap is produced mainly by a wet double decomposition process. In this process, an aqueous solution of the appropriate metal salt is added to an aqueous solution of sodium salt of a fatty acid, thereby precipitating the water-insoluble metallic salt. The process by-produces a large amount of water-soluble inorganic sodium salt. Accordingly, it is necessary that, after the reaction, the resulting metallic soap is fully washed with a large quantity of water to remove the inorganic sodium salt from the metallic soap. Moreover, as mentioned hereinabove, an aqueous dispersion of a metallic soap is produced by first preparing a metallic soap in this manner and then dispersing the metallic soap in water in the presence of a surfactant by means of a high performance agitator or a homogenizer. Under these circumstances, the conventional process for the preparation of aqueous dispersion of a metallic soap involves many steps and the production cost is inevitably expensive. In addition, the resulting dispersion not only comprises a metallic soap which has a large particle size and poor dispersibility but also has a high viscosity.

Other processes for the preparation of metallic soaps such as a dry direct fusion process or a wet direct precipitating process are also known. In the dry direct fusion process, a higher fatty acid is directly reacted with a metal compound at a high temperature. The process has a drawback that the resulting metallic soap suffers from thermal deterioration. The wet direct precipitating process is a process in which a fatty acid is first dispersed in water, and then a metal oxide or hydroxide is added to the dispersion so that the fatty acid reacts directly with the metal oxide or hydroxide. The process has an advantage that no water-soluble salt is by-produced contrast to the wet double decomposition process. The wet direct precipitating process has a further advantage that high temperature reactions are not needed so that the resulting metallic soap does not suffer from thermal deterioration, contrast to the dry direct fusion process.

However, according to the known wet direct precipitating process, it is difficult to complete the reaction between a higher fatty acid and a metal oxide. Therefore, the known process employs the metal oxide in excess so that the unreacted free higher fatty acid does not remain in the reaction mixture after the reaction. In consequence, the resulting aqueous dispersion of metallic soap has a low purity of the metallic soap.

SUMMARY OF THE INVENTION

The invention has been completed to solve the problems involved in the production of aqueous dispersion of metallic soaps as mentioned above. Accordingly, it is an object of the inventon to provide a process for preparing a low viscosity aqueous dispersion of higher fatty acid zinc salt having a small particle size in high yields.

The invention provides a process for preparing an aqueous dispersion of a higher fatty acid zinc salt which comprises adding a molten higher fatty acid to an aqueous dispersion of zinc oxide and reacting the higher fatty acid with the zinc oxide in the presence of a surfactant or a water-soluble polyvinyl alcohol with stirring while the aqueous dispersion or the reaction mixture is maintained at a tempereature that is higher than the melting point of the higher fatty acid used.

DETAILED DESCRIPTION OF THE PREFERRED EMBODIMENTS

The higher fatty acid used in the invention is a saturated or unsaturated monocarboxylic acid having from 8–30 carbons. Therefore, the higher fatty acid includes, for example, saturated fatty acids such as caprylic acid, caproic acid, capric acid, lauric acid, myristic acid, palmitic acid, stearic acid, arachic acid, behenic acid, lignoceric acid, cerotic acid, montanic acid or melissic acid; and unsaturated fatty acids such as oleic acid, linolic acid or linolenic acid. The higher fatty acid used in the invention may have hydroxyl, carbonyl or epoxy groups in the molecule. Thus, the higher fatty acid used further includes, for example, ricinoleic acid or 12-hydroxystearic acid. Among the above mentioned, myristic acid, palmitic acid or stearic acid, or a mixture of two or more is in particular preferred.

The surfactant used may be either cationic, nonionic or anionic. The cationic surfactant used includes, for example, higher alkylamine salts (such as acetates or hydrochlorides), ethylene oxide adducts to higher alkylamines, condensates of higher fatty acid and polyalkylenepolyamine (such as condensates of oleic acid and pentaethylenehexamine), salts of esters of higher fatty acids and alkanolamines (such as triethanolamine stearate formate (Soromin A-type available from B.A.S.F.(I.G.)), salts of higher fatty acid amides (such as stearamidoethyldiethylamine acetate (Sapamin A-type available from Ciba-Geigy), salts prepared by condensing higher fatty acids and aminoethylethanolamine under heat followed by bonding urea thereto and neutralizing the resulting condensate with acetic acid (such as Ahcovel A- or G-type cationic surfactants available from Ciba-Geigy), imidazoline-type cationic surfactants (such as 2-heptadecenylhydroxyethylimidazoline; Amine 0 available from Ciba-Geigy), (higher alkyl)trimethylammonium salts (such as lauryltrimethylammonium chloride), (higher alkyl) dimethylbenzylammonium salts (such as lauryldimethylbenzylammonium chloride), quaternary ammonium salts of higher fatty acid amides (such as products produced by quaternating tertiary amines derived from N,N-diethylethylenediamine and higher fatty acids with alkylating agents (such as Sapamin MS or Sapamin BCH available from Ciba-Geigy; Catanack SN available from American Cyanamid Co.) and alkylpyridinium salts.

The nonionic surfactant used includes, for example, ethylene oxide adducts to higher alcohols such as lauryl alcohol, ethylene oxide adducts to higher alkylphenols such as nonylphenol, ethyleneoxide adducts to fatty acids, ethylene oxide adducts to polyhydric alcohol farry acid esters, ethylene oxide adducts to higher alkylamines, ethylene oxide adducts to fatty acid amides, ethylene oxide adducts to fats and oils; ethylene oxide adducts to polypropylene glycol, glycerine fatty acid esters, pentaerythritol fatty acid esters, sorbitol or sorbitan fatty acid esters, sucrose fatty acid esters, polyhydric alcohol alkylether and fatty acid amides of alkanol amines.

The anionic surfactant used includes, for example, higher alcohol sulfates, higher alkyl ether sulfates, sulfonated oils, sulfonated fatty acid esters, sulfonated olefins, alkylbenzenesulfonates, alkylnaphthalenesulfonates, parrafin sulfonates, Igepon T (available from B.A.S.F.(I.G.), Aerosol OT available from American Cyanamid Co.) and higher alcohol phosphates.

Among the above mentioned, cationic surfactants are particularly preferred since the resulting higher fatty acid zinc salt is very fine and the resulting dispersion thereof has a very low viscosity.

A water-soluble polyvinyl alcohol may be used as a dispersant in place of the above mentioned surfactants. Namely, according to the invention, an aqueous dispersion of a higher fatty acid zinc salt is prepared by adding a molten higher fatty acid to an aqueous dispersion of zinc oxide and reacting the higher fatty acid with the zinc oxide in the presence of a surfactant or polyvinyl alcohol with stirring while the aqueous dispersion of zinc oxide or the reaction mixture is maintained at a temperature that is higher than the melting point of the higher fatty acid used.

Zinc oxide is used in an amount of 0.45–0.65 moles per mole of the higher fatty acid used. The surfactant or polyvinyl alcohol is used usually in an amount of 2–15% by weight, preferably in an amount of 5–10% by weight, based on the higher fatty acid used. The amount of water used as a reaction medium is not specifically limited, but it is usually in the range of one to three times the weight of the resulting higher fatty acid zinc salt.

In a preferred embodiment of the invention, zinc oxide is first dispersed in water, and the dispersion is heated to and maintained at a temperature that is higher than the melting point of the higher fatty acid used, and then a molten higher fatty acid is added gradually to the dispersion with effective stirring, thereby reacting the higher fatty acid with zinc oxide in the presence of a surfactant or polyvinyl alcohol.

It is preferred that after the completion of the addition of the molten higher fatty acid, the resulting reaction mixture is stirred over a period of further several hours while the reaction mixture is maintained at a temperature that is higher than the melting point of the higher fatty acid used. The upper limit of the reaction temperature is not specifically limited, however, it is usually about 110° C. The reaction is carried out usually under normal pressures, however, it may be carried out under reduced or increased pressures, if necessary.

According to the invention, the higher fatty acid zinc salt is obtained usually in a yield as high as 95–99%, and there is obtained in a stable manner a 30–50% concentration aqueous dispersion of higher fatty acid zinc salt having an average particle size of 0.5–5 $\mu$m, in a preferred embodiment, an average particle size of 1.0–2.0 $\mu$m.

As set forth above, the process of the invention readily provides an aqueous dispersion of higher fatty acid zinc salt having a small particle size in high yields. The dispersion is stable and has a low viscosity. The aqueous dispersion is suitable for use as a lubricant incorporated in a coating for the production of coated paper to prevent dusting or flouring, or as a viscosity stabilizer for the coating.

The invention will be now described with reference to examples, however, the examples are illustrative only and the invention is not limited thereto.

EXAMPLE 1

5.95 g of zinc oxide was dispersed in 90 g of distilled water while 2.4 g of a condensate of oleic and pentaethylenehexamine (cationic surfactant) was dissolved therein. 35 g of stearic acid (m.p.: 56° C.) was heated to about 70° C. and the resulting molten stearic acid was added to the aqueous mixture gradually. Thereafter, the reaction mixture was stirred for three hours while it was maintained at a temperature of 60° C.

After the reaction, the reaction mixture was allowed to cool to normal temperatures, thereby providing an aqueous dispersion of zinc stearate. The yield of zinc stearate was found to be 95.7%. The dispersion was found to contain zinc stearate in 41.2% by weight and have a viscosity of 150 centipoises at 25° C. The average particle size of the zinc stearate was found to be 1.3 $\mu$m.

EXAMPLE 2

An aqueous dispersion of zinc stearate was prepared in the same manner as in Example 1 except that 2.8 g of a condensate of palmitic acid and aminoethylethanolamine; Ahcovel A-type) was used as a cationic surfactant. The yield of zinc stearate was found to be 96.1%.

The dispersion was found to contain zinc stearate in 39.4% by weight and have a viscosity of 130 centipoises at 25° C. The average particle size of the zinc stearate was found to be 1.0 $\mu$m.

EXAMPLE 3

An aqueous dispersion of zinc stearate was prepared in the same manner as in Example 1 except that a mixture of 1.0 g of a condensate of oleic acid and pentaethylenehexamine and 1.6 g of a condensate of palmitic acid and aminoethylethanolamine; Ahcovel A-type) was used as a cationic surfactant. The yield of zinc stearate was found to be 95.8%.

The dispersion was found to contain zinc stearate in 40.5% by weight and have a viscosity of 110 centipoises at 25° C. The average particle size of the zinc stearate was found to be 1.1 $\mu$m.

EXAMPLE 4

An aqueous dispersion of zinc stearate was prepared in the same manner as in Example 1 except that 3.0 g of dodecyltrimethylammonium chloride was used as a cationic surfactant. The yield of zinc stearate was found to be 99.1%.

The dispersion was found to contain zinc stearate in 40.2% by weight and have a viscosity of 110 centipoises at 25° C. The average particle size of the zinc stearate was found to be 1.2 $\mu$m.

EXAMPLE 5

An aqueous dispersion of zinc stearate was prepared in the same manner as in Example 1 except that 4.0 g of an ethylene oxide (6 mole) adduct to lauryl alcohol (nonionic surfactant) was used in place of the cationic surfactant. The yield of zinc stearate was found to be 99.0%.

The dispersion was found to contain zinc stearate in 40.1% by weight and have a viscosity of 350 centipoises at 25° C. The average particle size of the zinc stearate was found to be 2.0 $\mu$m.

EXAMPLE 6

An aqueous dispersion of zinc stearate was prepared in the same manner as in Example 1 except that a mixture of 2.0 g of an ethylene oxide (6 mole) adduct to lauryl alcohol (nonionic surfactant) and 1.8 g of an ethylene oxide (10 mole) adduct to nonylphenol (nonionic surfactant) was used in place of the cationic surfactant. The yield of zinc stearate was found to be 99.2%.

The dispersion was found to contain zinc stearate in 41.3% by weight and have a viscosity of 270 centipoises at 25° C. The average particle size of the zinc stearate was found to be 2.8 μm.

EXAMPLE 7

An aqueous dispersion of zinc stearate was prepared in the same manner as in Example 1 except that 2.0 g of sodium dodecyl sulfate (anionic surfactant) was used in place of the cationic surfactant. The yield of zinc stearate was found to be 97.3%.

The dispersion was found to contain zinc stearate in 40.9% by weight and have a viscosity of 410 centipoises at 25° C. The average particle size of the zinc stearate was found to be 2.3 μm.

EXAMPLE 8

An aqueous dispersion of zinc stearate was prepared in the same manner as in Example 1 except that 2.35 g of polyvinyl alcohol having a saponification degree of about 88 mole % and an average polymerization degree of 800 (PA-05 available from Shin-etsu Poval) was used in place of the cationic surfactant. The yield of zinc stearate was found to be 99.3%.

The dispersion was found to contain zinc stearate in 38.7% by weight and have a viscosity of 290 centipoises at 25° C. The average particle size of the zinc stearate was found to be 1.3 μm.

What is claimed is:

1. A process for preparing an aqueous dispersion of a higher fatty acid zinc salt for use as a lubricant incorporated in a coating for the production of coated paper to prevent dusting or flouring or as a viscosity stabilizer for the coating, which consists essentially of adding a molten higher fatty acid to an aqueous dispersion of zinc oxide and reacting the higher fatty acid with the zinc oxide in the presence of a cationic surfactant in an amount of 2–15% by weight based on the higher fatty acid with stirring while the aqueous dispersion is maintained at a temperature that is higher than the melting point of the higher fatty acid used, thereby providing a 30–50% concentration aqueous dispersion of a higher fatty acid zinc salt having an average particle size of 1.0–2.0 μm in a yield of 95–99% and the viscosity of said dispersion is 110 to 150 centipoise.

2. The process as claimed in claim 1 wherein zinc oxide is used in an amount of 0.45–0.65 moles per mole of the higher fatty acid.

3. The process as claimed in claim 1 wherein the cationic surfactant is used in an amount of 5–15% by weight based on the higher fatty acid.

4. The process as claimed in claim 1 wherein the higher fatty acid is stearic acid.

5. A process for preparing an aqueous dispersion of a higher fatty acid zinc salt for use as a lubricant incorporated in a coating for the production of coated paper to prevent dusting or flouring or as a viscosity stabilizer for the coating, which consists essentially of adding a molten higher fatty acid to an aqueous dispersion of zinc oxide and reacting the higher fatty acid with the zinc oxide in the presence of a water-soluble polyvinyl alcohol in an amount of 2–15% by weight based on the higher fatty acid with stirring while the aqueous dispersion is maintained at a temperature that is higher than the melting point of the higher fatty acid used, thereby providing a 30–50% concentration aqueous dispersion of a higher fatty acid zinc salt having an average particle size of 1.0–2.0 μm in a yield of 95–99%.

6. The process as claimed in claim 5 wherein zinc oxide is used in an amount of 0.45–0.65 moles per mole of the higher fatty acid.

7. The process as claimed in claim 5 wherein the polyvinyl alcohol is used in an amount of 5–15% by weight based on the higher fatty acid.

8. The process as claimed in claim 5 wherein the higher fatty acid is stearic acid.

\* \* \* \* \*